United States Patent [19]

Hudgell

[11] 4,107,605

[45] Aug. 15, 1978

[54] EDDY CURRENT FLAW DETECTOR UTILIZING PLURAL SETS OF FOUR PLANAR COILS, WITH THE PLURAL SETS DISPOSED IN A COMMON BRIDGE

[75] Inventor: Robert John Hudgell, Warrington, England

[73] Assignee: British Gas Corporation, England

[21] Appl. No.: 731,892

[22] Filed: Oct. 13, 1976

[30] Foreign Application Priority Data

Oct. 15, 1975 [GB] United Kingdom ............ 42162/75

[51] Int. Cl.² ........................................... G01R 33/12
[52] U.S. Cl. ................... 324/220; 324/227; 324/238
[58] Field of Search .................................. 324/37, 40

[56] References Cited

U.S. PATENT DOCUMENTS

| 3,500,181 | 3/1970 | Jackson | 324/37 |
|---|---|---|---|
| 3,518,533 | 6/1970 | Arnelo | 324/37 |
| 3,568,049 | 3/1971 | Barton | 324/37 |
| 3,916,302 | 10/1975 | Madewell | 324/37 |

FOREIGN PATENT DOCUMENTS

| 853,842 | 10/1970 | Canada | 324/37 |
|---|---|---|---|
| 1,161,106 | 8/1969 | United Kingdom | 324/40 |

*Primary Examiner*—Robert J. Corcoran
*Attorney, Agent, or Firm*—Larson, Taylor and Hinds

[57] ABSTRACT

The invention relates to a method and apparatus for the non-destructive testing of pipelines and is particularly concerned with the use of alternating eddy currents to investigate anomalies in the walls of pipelines of ferromagnetic material. A probe includes sensing coils which are connected in a bridge circuit. By employing spiral coils, placed with their axes normal to the surface of the pipeline wall, the apparatus is made less sensitive to variations in the spacing of the probe and sample. Use of biassing magnetic fields permits the detection of anomalies in pipeline walls of thickness substantially greater than the normal eddy current penetration depth.

2 Claims, 21 Drawing Figures

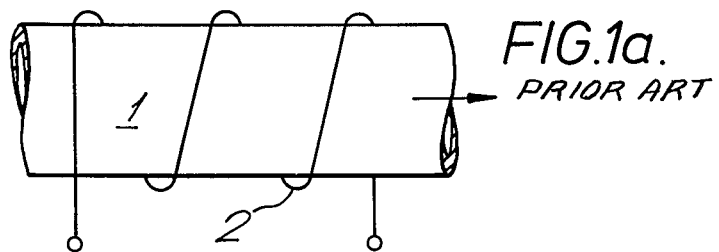
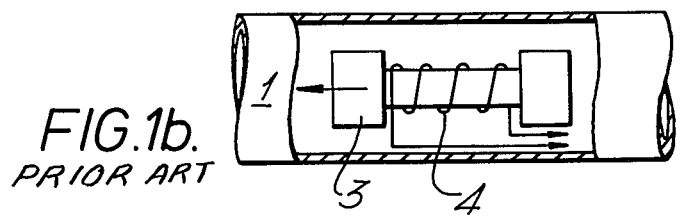
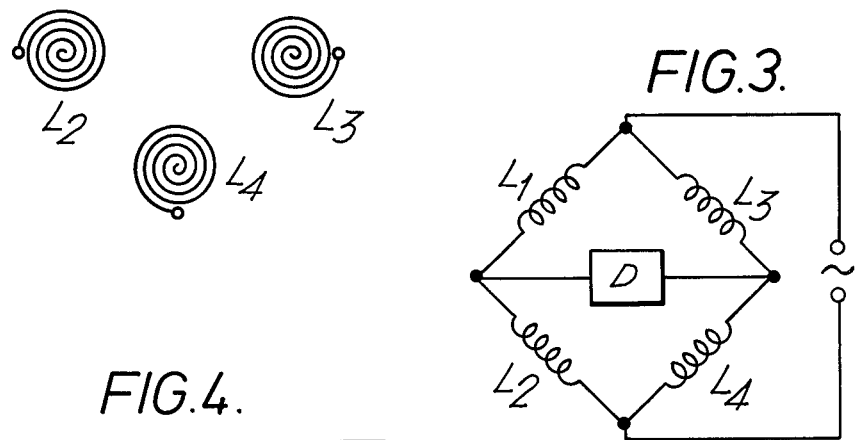
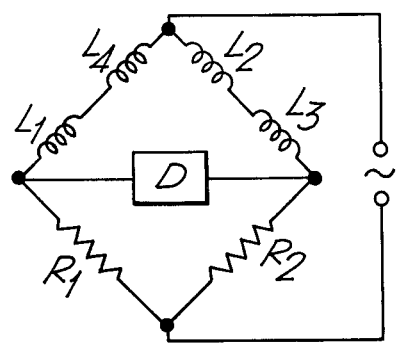

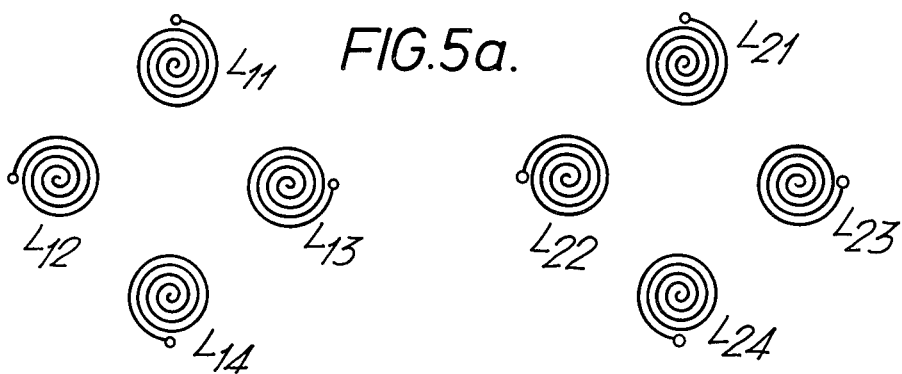
FIG.5a.
FIG.5b.
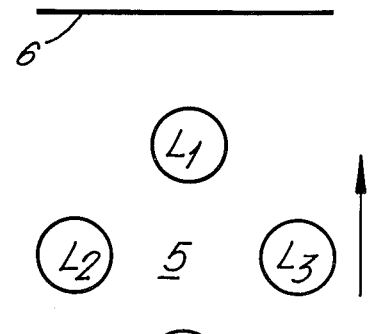
FIG.6a.
FIG.6b.
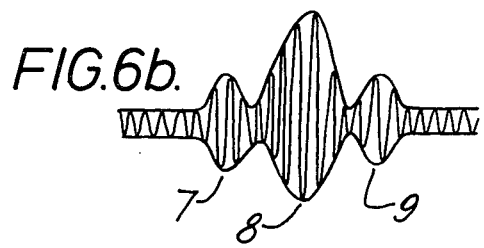
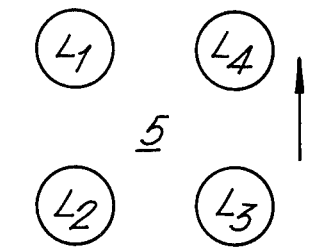
FIG.7a.
FIG.7b.
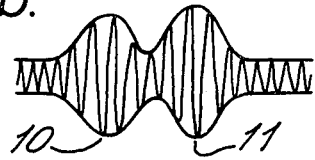

EDDY CURRENT FLAW DETECTOR UTILIZING PLURAL SETS OF FOUR PLANAR COILS, WITH THE PLURAL SETS DISPOSED IN A COMMON BRIDGE

This invention relates to the non-destructive testing of metallic pipelines, and in particular to testing methods based on the measurement of changes in induced eddy currents.

Eddy current testing is utilised as a non-destructive testing means for tubes and small-diameter pipes which may either be seamless or seam-welded. With known methods, the tube or pipe is usually placed in the centre of a circular coil. By passing an alternating current through this coil, an eddy current is induced in the tube. This eddy current, in turn, produces an additional alternating magnetic field in the vicinity of the tube. Discontinuities or inhomogeneities in the metal cause variations in the eddy current and hence changes in the secondary magnetic field. This produces an electrical signal which may be detected and displayed on an oscilloscope or other measuring or alarm instrument. Instead of encircling coils, an internal probe (or bobbin) may be passed through the centre of the tube, or probe coils may be used on the outside. Manual scanning with a probe coil is also performed.

Eddy current testing methods have the advantage that they require only compact ancillary equipment to perform the measurements, but the prior art techniques described above have the disadvantage that they are not readily applicable to the in situ measurement of pipelines. In order to overcome this drawback a new method of eddy current measurement of pipelines has been devised.

According to the present invention there is provided a non-destructive method of testing metallic pipelines comprising the induction of eddy currents in a region of the pipeline, probing said region with a plurality of sensing coils to detect said eddy currents and comparing the currents detected by said coils in order to derive an indication of a fault in said region of the pipeline.

Preferably, each of said coils is included within an arm of a normally balanced bridge circuit, the out-of-balance current of said bridge being used to provide an indication of a fault in said region of the pipeline.

According to a particular embodiment of the invention, magnetic biassing means are provided to create a magnetic field in the vicinity of the region of the pipeline under test whilst the eddy current measurements are being carried out.

The invention will now be described with reference to the accompanying drawings in which FIGS. 1a and 1b shows in diagrammatic section, prior art methods of eddy current testing FIG. 2 is a diagram showing an arrangement of eddy current sensor coils according to one aspect of the invention FIG. 3 is a simple bridge circuit suitable for the coil arrangement of FIG. 2

FIG. 4 is an alternative bridge circuit diagram suitable for the coil arrangement of FIG. 2

FIGS. 5a and 5b show how two sets of sensor coils may be combined into one bridge circuit FIGS. 6a and 6b to 8 show typical out-of-balance signals produced when a line surface-breaking defect is scanned by sensing coils connected in a bridge circuit in accordance with an embodiment of the invention FIG. 9 is a block diagram showing a method of generating and measuring eddy current signals according to an aspect of the invention FIG. 10 is a block diagram of a multi-channel sensor suitable for scanning a relatively large area of pipeline surface FIG. 11 is the circuit diagram of a specific multi-channel sensor of the type illustrated in FIG. 10

FIG. 14 shows the experimental arrangement used to obtain the trace shown in FIG. 13a.

Figure 8:
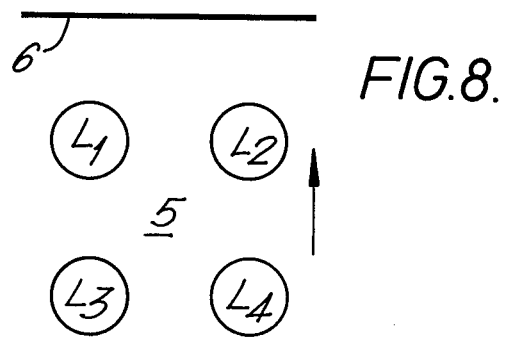

Referring now to FIGS. 1a and 1b of the drawings, these illustrate principles employed in existing eddy current systems for inspecting cylindrical products, such as pipes.

In the system illustrated in FIG. 1a, a pipe is passed through the centre of a coil 2. An alternating current is passed through the coil, inducing an eddy current in the tube. This eddy current in turn produces an auxiliary magnetic field in the vicinity of the tube. Discontinuities in the base metal or weld cause changes in the secondary magnetic field which varies the impedance of the coil. The changes in impedance may be sensed and displayed on a chart recorder, oscilloscope or other measuring instrument.

In another prior art system shown in FIG. 1b, a soft iron bobbin 3 carrying a coil 4 is passed down a tube 1 under test. An alternating current is passed through the coil and changes in impedance are sensed as above.

The disadvantage of the systems described above is that they are mainly applicable to precision components such as drawn tubes and are not applicable to irregular and asymmetric products such as piping used for the transport of gas. Furthermore, the method employing an encircling coil is not applicable to in situ measurement.

To provide a method of testing irregular pipes in situ, a particular form of sensor has been devised. One embodiment employs an arrangement of sensing coils as illustrated in FIG. 2. Four sensing coils $L_1$, $L_2$, $L_3$ and $L_4$, which preferably are of similar physical construction are connected in a bridge circuit as shown in FIG. 3. The coils may be flat or profiled to conform to the surface under test. A signal is applied across the bridge and the out-of-balance current is detected by a detector circuit D. In the initial state the bridge is balanced, the inductances of the coils being chosen to satisfy the relationship $$L_1 L_4 = L_2 L_3$$

Preferably all four coils have the same number of turns and equal diameters, and are so spaced that their centres are at the corners of a square.

In an alternative circuit shown in FIG. 4, coils $L_1$ and $L_4$ are connected in series in one arm of a bridge and coils $L_2$ and $L_3$ are connected in series in another arm, the arrangement being equivalent to that of twin sensing coils. Balance is achieved by means of resistors $R_1$ and $R_2$.

Yet a further arrangement, this time employing two sets of sensing coils ($L_{11}$, $L_{12}$, $L_{13}$, $L_{14}$) and ($L_{21}$, $L_{22}$, $L_{23}$, $L_{24}$) shown in FIG. 5a may be connected in a bridge as shown in FIG. 5b. This arrangement has the advantage that it can scan a larger area of pipe in a single pass, or economise in the number of channels required in the data processor.

When the eddy current sensor shown in FIG. 2 is placed near a conducting surface, each coil induces eddy currents in the surface. The eddy currents flow in a circular path in such a direction that the alternating magnetic field produced by the eddy currents opposes that from the coil. The electromagnetic interaction between the coils and the conducting surface under test does not alter the balance of the bridge provided all coils are equally affected, although the electrical characteristics of each coil will change. For this reason, a bridge probe is not sensitive to "lift-off", which will produce only a second-order effect.

However, imperfections will cause interruptions in the eddy currents by increasing the path impedance in their vicinity. FIGS. 6 to 8 illustrate the effect of scanning a line defect orientated in a number of different ways with respect to the set of probe coils connected in the bridge circuit of FIG. 3.

The output signal from the coils 5 when scanning a line defect 6 which could be a crack or gouge is shown in FIG. 6b. The initial output is low, corresponding to the residual noise. As coil $L_1$ traverses the defect the signal level rises to a peak 7 and falls again. As coils $L_2$, $L_3$ traverse the defect a larger peak 8 is obtained, and finally, when coil $L_4$ traverses the defect another small peak 9 results.

When the defect 6 is scanned by the sensor coils in the direction shown by the arrow in FIG. 7, two peaks results, the first as $L_1$ and $L_4$ traverse the defect, and the second as $L_2$ and $L_3$ traverse the defect (10,11 resp.).

No response is obtained when the sensing coils scan a line defect in the direction indicated by the arrow in FIG. 8 since $L_1$ and $L_2$, and $L_3$ and $L_4$ are influenced simultaneously and the condition of balance $$L_1L_4 = L_2L_3$$

remains.

By suitable orientation of sensing coils it is possible to derive comprehensive information about the size and location of faults in the surface under test.

The bridge output signal is a low-frequency modulation envelope containing the high frequency of the energising oscillator. The frequency of modulation is a function of the spacing of the coils along the direction of scan and the velocity of scan. The amplitude of the modulation depends on the sensitivity of the coil arrangement to the size and type of defect and the separation between the sensor coils and the surface under test.

Figure 9:
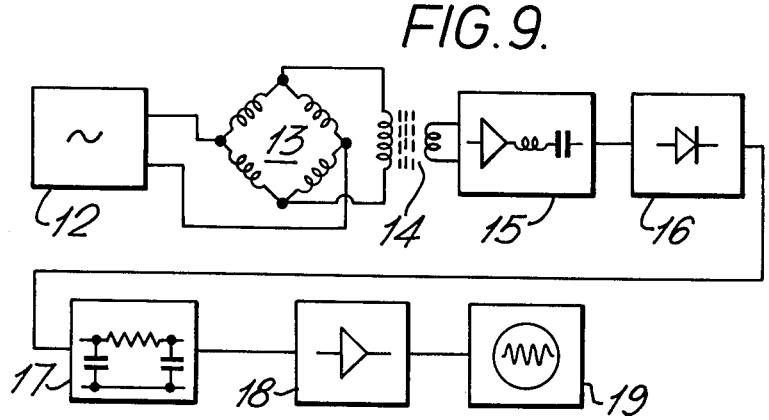

FIG. 9 is a block diagram showing the elements in a typical eddy current testing system in accordance with an aspect of the invention. An eddy current probe circuit 13 is energised by means of an oscillator 12. Out-of-balance signals are fed by way of an impedance matching transformer 14 to a tuned amplifier 15 and a demodulator 16. The low frequency component is removed by means of a low-pass filter 17, which is designed to pass only those signals in the modulation envelope which are created by sensed defects. For applications where the scanning speed is not constant, as for on-line inspection applications, the low-pass filter must be designed to pass a wide band of frequencies. The low frequency output is further amplified by an amplifier 18 and is displayed on a display device 19 which may be an oscilloscope.

Figure 10:
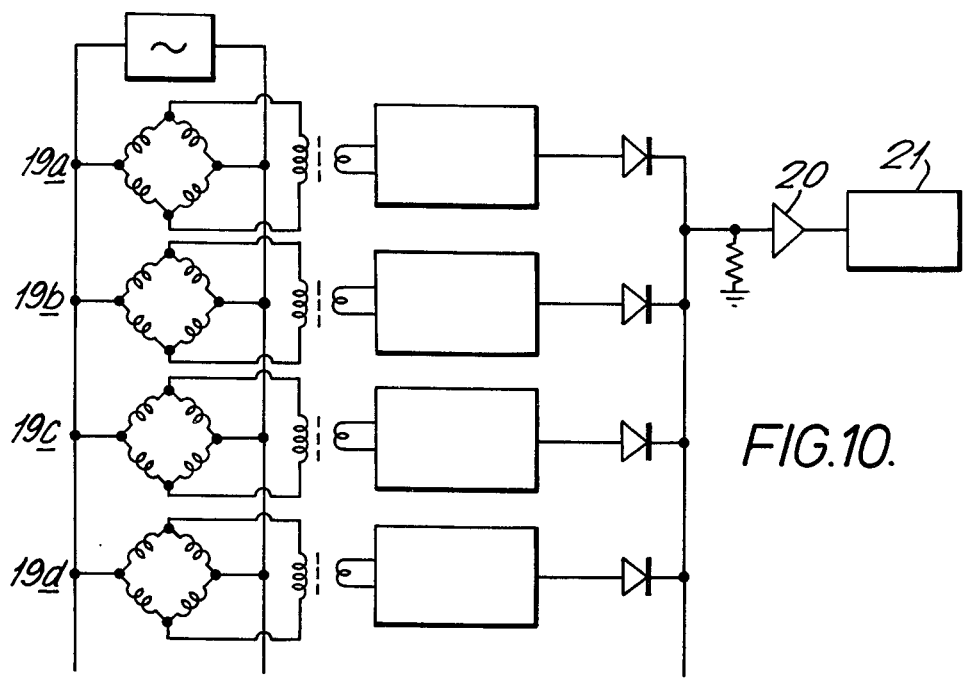

FIG. 10 is a block diagram of a data compression system suitable for recording the output of a plurality of scanning probes on a single channel of a data recording apparatus such as a tape recorder. This comprises a plurality of sensor channels 19a to 19d of the type shown in FIG. 9, feeding into a recording amplifier 20 and a tape head 21.

Figure 11:
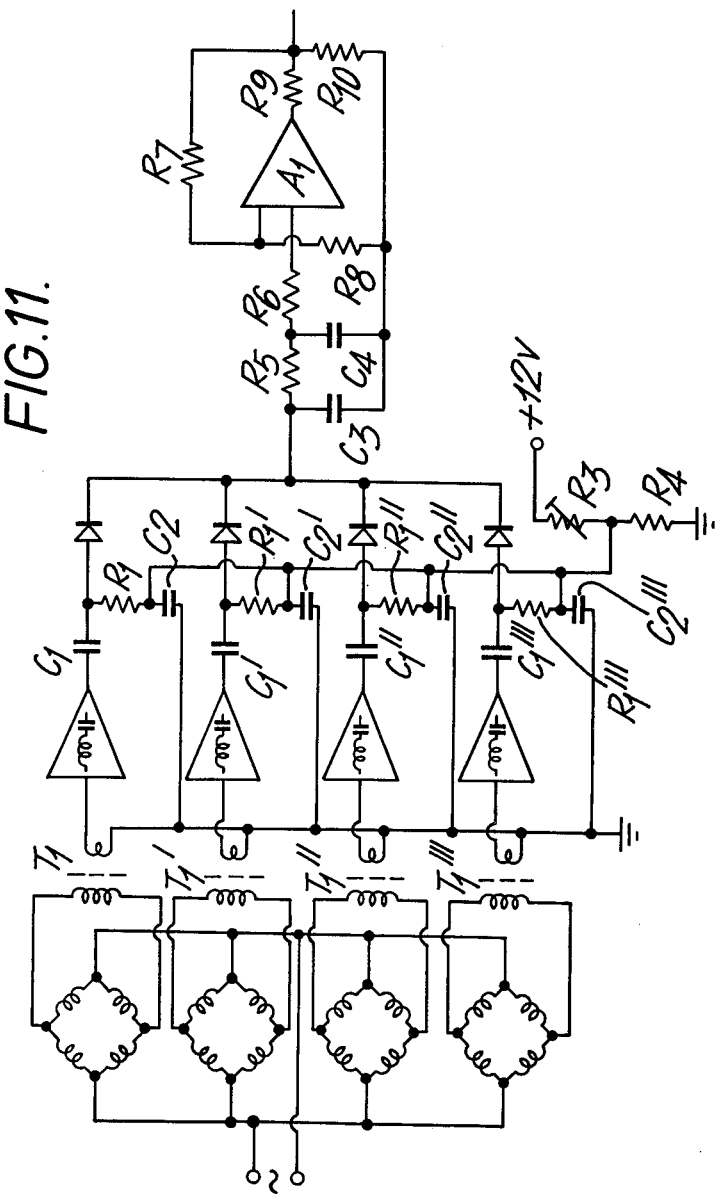
Figure 12A:
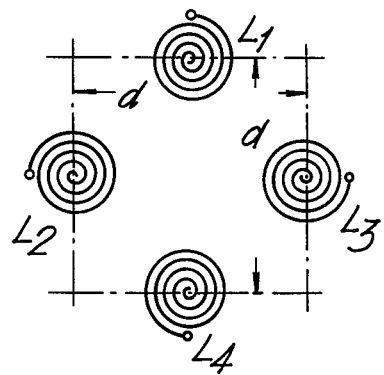
FIGS. 12a to 12d show details of parts of the circuit shown in FIG. 11
Figure 12B:
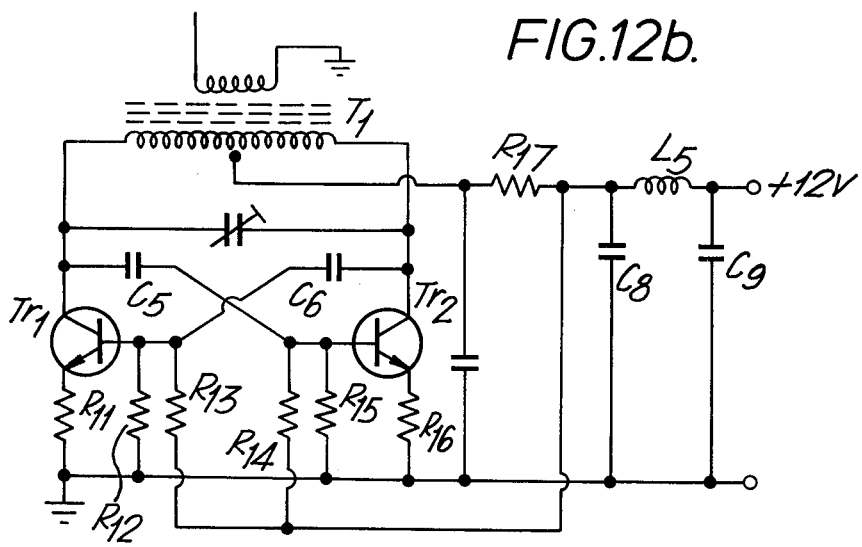
Figure 12C:
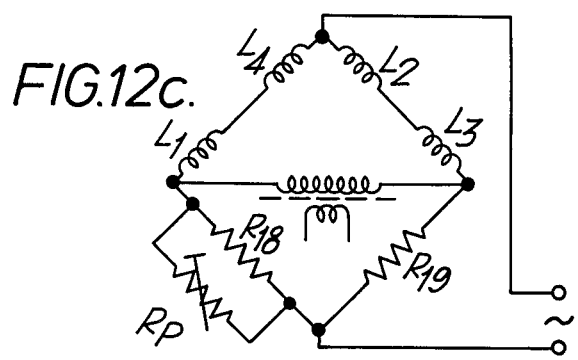
Figure 12D:
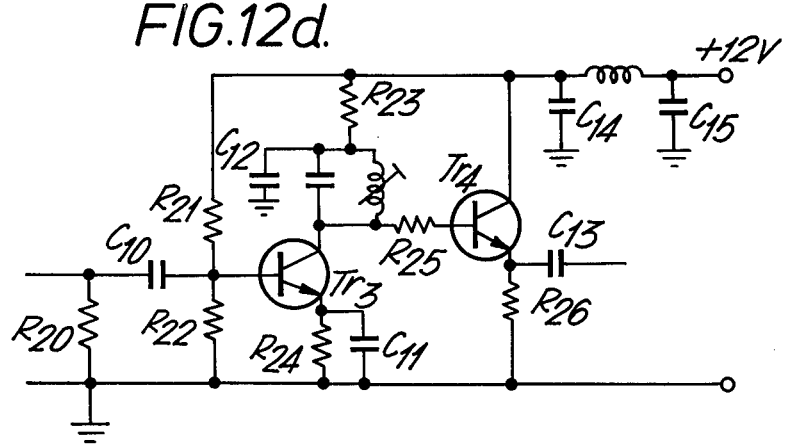

A practical embodiment of the invention is illustrated in FIG. 11 which shows a four-channel eddy current probe system. Detailed circuits of the component circuit elements are depicted in FIG. 12 which shows the probe coil arrangement (FIG. 12a), the bridge circuit (FIG. 12c), the energising oscillator (FIG. 12b) and the tuned amplifier (FIG. 12d). Component values are given in Table 1.

Eddy current sensors for one channel consist of four flat spiral coils ($L_1$, $L_2$, $L_3$, $L_4$) 18mm in diameter of 38 SWG diameter wire having centres at the corners of a square of 27mm diagonal. Four such eddy current sensors, each connected in a simple bridge circuit, are mounted on a shoe with a non-conducting front end, suitable for pulling through a pipe. Each bridge circuit is balanced by means of a padder resistor $R_p$.

The output from a 1 MHz oscillator is connected to the four bridge circuits in parallel, the output of each bridge being connected to a tuned amplifier. All four channels are connected by way of a low-pass filter and an operational amplifier to a recorder.

Figure 13:
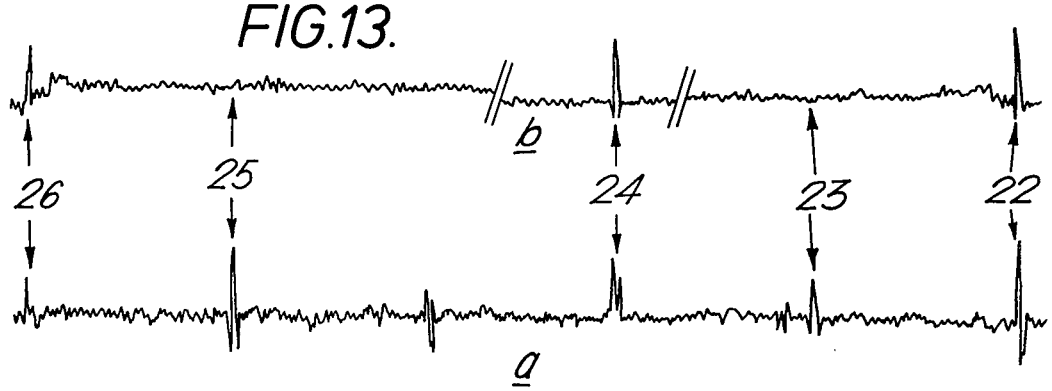
FIGS. 13a and 13b are oscilloscope traces of typical signals from an eddy current sensor in accordance with an embodiment of the invention.
Figure 14:
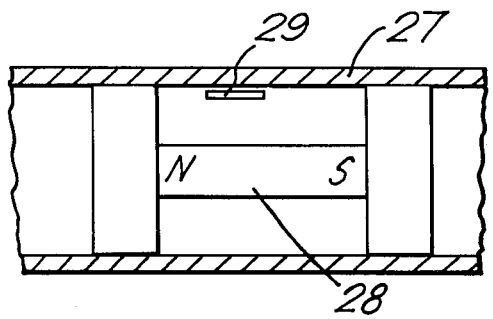

A typical recording is illustrated in FIG. 13a which shows a number of characteristic peaks which were produced successively by the flange 22, 50% external pits 23, 25% internal pits 24, 25% external gouge 25 and a weld 26 as the system was pulled through a section of the pipe being magnetised, as in the arrangement of FIG. 14, by a biassing magnet 28, the eddy current coils being placed between the poles.

A similar result (FIG. 13b) but indicating only internal defects is obtained in the absence of a biassing magnet, providing the basis for distinguishing internal from external defects by comparing outputs from systems with and without biassing fields.

The eddy current system detects faults as a change in permeability at the inside surface. The presence of a defect concentrates magnetic flux within the steel beneath and around the defect, resulting in a permeability change detected by an eddy current coil passing near it.

Optimum sensitivity of the eddy current bridge to corrosion pits has been found to occur when the diameter of the pits is equal to that of the coils. Loss of sensitivity occurs for much smaller pits to the point where the sensor is unlikely to detect pits of diameter less than one fifth of the diameter of the coil, irrespective of depth. The sensitivity to large areas of corrosion depends on the rate of change of depth of the sides of the area corroded and anomalies within this area.

The method has been found to be of particular value in the detection of surface laminations, scabs and loose metallic material. It is also sensitive to cracks which are suitably oriented with respect to the bridge circuit.

A particular advantage is that, unlike existing detection systems, the eddy current sensor and bridge circuits do not produce defect-like signals when the separation between the coils and the surface under test is varied. (This is commonly known as lift-off.) The reason for this is that, although the absolute magnitude of the inductances of the coils will be reduced, to a first order approximation the relationship $$L_1L_4 = L_2L_3$$

will still be satisfied.

It will be apparent to those skilled in the art that modifications to the above embodiment may be made whilst still remaining within the scope of the invention. For example, phase sensitive detectors may have advantages in certain instances, whilst to permit the detection of low-level faults, auto-correlation techniques may, with advantage, be employed.

TABLE 1

| | R (ohms) | | | | |
|---|---|---|---|---|---|
| 1 | 10K | 11 | 100 | 21 | 3.3K |
| 2 | 10K | 12 | 1.5K | 22 | 330 |
| 3 | 10K | 13 | 10K | 23 | 1.5K |
| 4 | 150 | 14 | 10K | 24 | 100 |
| 5 | 15K | 15 | 1.5K | 25 | 150 |
| 6 | 220K | 16 | 100 | 26 | 1K |
| 7 | 2.5M | 17 | 100 | | |
| 8 | 270K | 18 | 470 | | |
| 9 | 51 | 19 | 470 | | |
| 10 | 1.2K | 20 | 47 | | |
| | C (farads) | | | | |
| 1 | 470p | 11 | 220p | | |
| 2 | 10n | 12 | 10n | | |
| 3 | 1.5n | 13 | 470p | | |
| 4 | 1.5n | 14 | 10n | | |
| 5 | 620p | 15 | 10n | | |
| 6 | 620p | | | | |
| 7 | 10n | | | | |
| 8 | 10n | | | | |
| 9 | 10n | | | | |
| 10 | 10n | | | | |
| | Tr (type) | | | | |
| 1 | BLY 33 | | | | |
| 2 | BLY 33 | | | | |
| 3 | 2N929 | | | | |

TABLE 1-continued

| 4 | 2N4427 |
|---|---|

We claim:

1. Apparatus for the non-destructive testing of metallic pipelines having a body adapted to tranverse a pipeline, a probe bearing a plurality of sets of four substantially planar spiral coils mounted on said body by probe mounting means for holding said coils each with its axis substantially normal to a surface of a pipeline while urging said probe towards said surface, coil energizing means for energizing said coils by the passage of an alternating current therethrough, magnetic biasing means, mounted on said body, for producing a magnetic field in the vicinity of said plurality of sets of coils, and detector means mounted on said body, the shape of the coils substantially conforming to the shape of the surface of the pipeline under test, each coil of each said set of four coils being arranged with its respective axis at a respective corner of a square and said plurality of sets of coils being connected in a single bridge circuit with each coil of each set being disposed in a different arm of the bridge with said detector means connected across said bridge circuit so that the sensitivity of said detector means to differences in spacing of said coils and the surface under test is reduced.

2. Apparatus for the non-destructive testing of metallic pipelines according to claim 1, wherein said plurality of sets of coils is connected by means of said single bridge circuit to one channel of a data processor.

* * * * *